Sept. 18, 1951 W. KORDES Plant Pat. 1,036
ROSE PLANT
Filed July 18, 1950
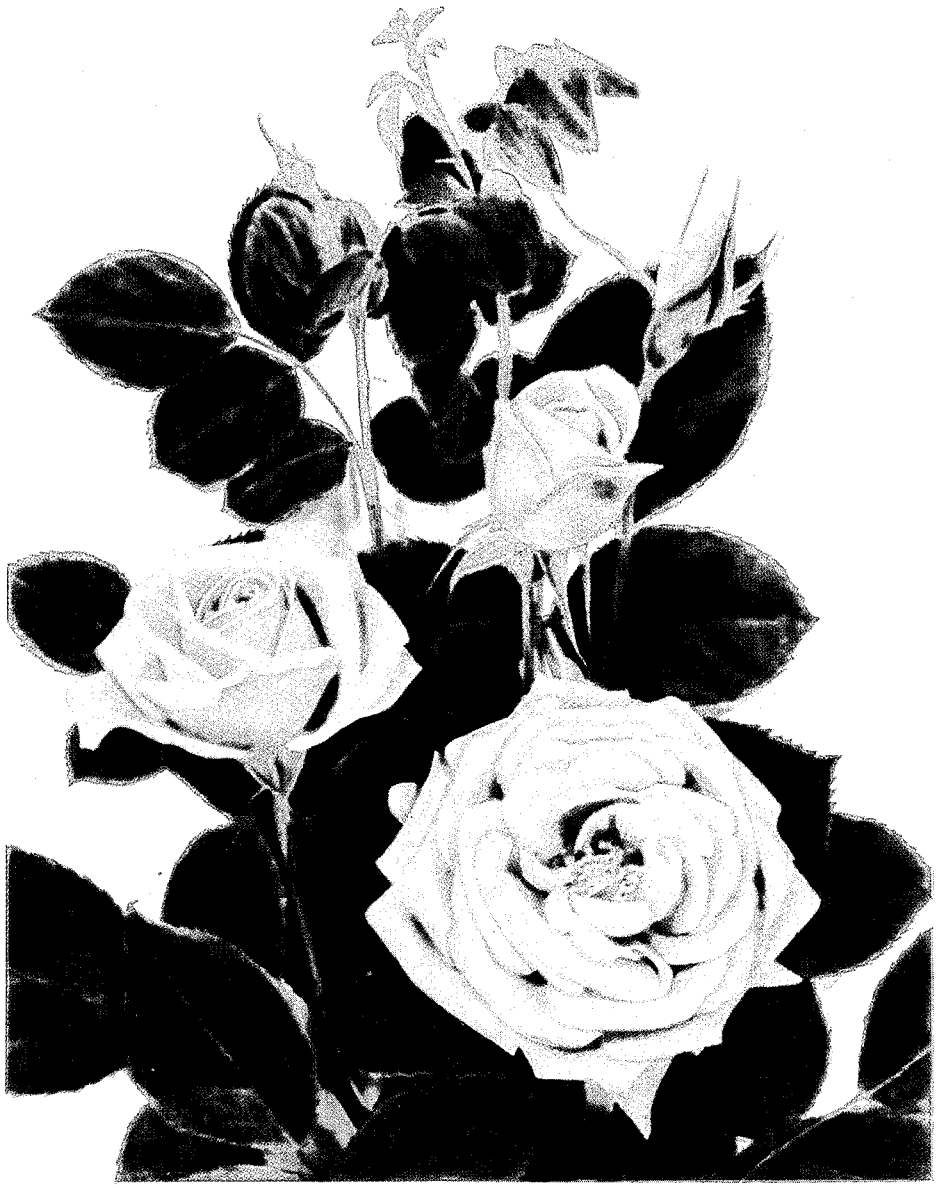
Inventor
Wilhelm Kordes
By: Robert Cobb
Attorneys.

Patented Sept. 18, 1951

Plant Pat. 1,036

UNITED STATES PATENT OFFICE 1,036

ROSE PLANT

Wilhelm Kordes, Holstein, Germany, assignor to Jackson & Perkins Company, Newark, N. Y., a corporation of New York Application July 18, 1950, Serial No. 174,547

1 Claim. (Cl. 47—61)

This invention relates to a new and distinct variety of rose plant of the large-flowered polyantha class, originating as a self-seedling of an unnamed seedling of "Crimson Glory" (Plant Patent No. 105) × "Baby Chateau" (unpatented).

The outstanding and primary feature of importance of this new variety is the color of the flowers which is new and unusual, and completely distinct from that of any other rose of which I am aware. This unique color, which may be generally described as Spectrum Red overcast with Scarlet Red, is definitely clearer and sharper in tone than in its parent. The cupped form of the blooms of the new variety particularly accentuates the sharpness of the color, while the petaloids in the center have a deep cut at the top with a white streak through the center which is distinctly different from any other rose.

The foregoing characteristics are combined with freedom of growth and clustered habit of bloom in a true floribunda manner, hardiness and disease resistance, which together make a sharp and distinct impression and contribute to the unique characteristics of this new variety.

Asexual reproduction of the new variety by budding at Newark, New York, and at Pleasanton, California, shows that the foregoing characteristics come true to form and are fixed and transmitted through succeeding propagations.

The accompanying drawing shows specimens of the foliage and blooms of this new variety, with the flowers in different stages of development from small bud to full-open bloom.

The following is a detailed description of the new variety, with color terminology in accordance with Ridgway's Color Standards and Nomenclature:

Parentage: Seedling. A self-seedling of an unnamed seedling of "Crimson Glory" × "Baby Chateau."

Classification:

*Botanic.*—Large flowered polyantha.

*Commercial.*—Floribunda.

*Flower*

(Observations made in greenhouses at Newark, New York, in the afternoon in the month of December 1949.)

Blooming habit: Recurrent—continuous.

Bud:

*Size.*—Medium.

*Form.*—Urn. Is not affected by wet or hot weather.

*Color.*—When sepals first divide—Victoria Lake, Plate 1. When petals begin to unfurl—Spectrum Red, Plate 1, lightly overcast with Nopal Red, Plate 1. When half blown—inside of petals—Spectrum Red, Plate 1, lightly overcast with Scarlet Red, Plate 1.

*Sepals.*—Slightly branched. Curl back when petals begin to unfurl. Color—inside: Courge Green, Plate 17; outside: Parrot Green, Plate 6.

*Calyx.*—Shape—oblong. Size—broad. Aspect—smooth. Odor when rubbed—none. Color—Lettuce Green, Plate 5.

*Peduncle.* — Length — medium. Aspect—smooth. Color—Biscay Green, Plate 17. Strength — erect; slender.

*Opening.*—Bud opens up well. Is not affected by adverse weather conditions.

Bloom:

*Size.*—Large. Average size when fully expended, 4 inches.

*Borne.*—Singly in irregular clusters.

*Stems.*—Medium length; strong.

*Form.*—When first open—cupped. Permanence—retains its form to the end.

*Petalage.*—Double (full but open center). Number of petals under normal conditions, 35.

*Color.*—Center of flower—Rose Red, Plate 12, overlaid with Scarlet, Plate 1. Outer petals—Scarlet, Plate 1, lightly overcast with Spectrum Red, Plate 1. Base of petals (aiglet)—Light Chalcedony Yellow, Plate 17, which suffuses into the Spectrum Red, Plate 1, of the petal. Inside of petals—Spectrum Red, Plate 1, lightly overcast with Scarlet, Plate 1. Reverse of petals—Scarlet Red, Plate 1. General tonality from a distance—Spectrum Red, Plate 1.

*Discoloration.*—General tonality at end of first day—Spectrum Red, Plate 1. Second day—Spectrum Red, Plate 1, overcast with Scarlet, Plate 1. Third day—Spectrum Red, Plate 1, lightly overcast with Scarlet, Plate 1.

Petals:

*Texture.*—Thick. Is not affected by wet or hot weather.

*Appearance.*—Inside — velvety. Outside—satiny.

*Form.*—Oval.

*Arrangement.*—Imbricated (regularly arranged shinglelike). Petaloids in center—few; large. Each petaloid is deeply cut on the top which is characteristically marked with White, Plate 53, from the center of the cut to the aiglet.

*Persistence.*—Drop off cleanly.

*Fragrance.* — Moderate. Nature — old-fashioned tea (average hybrid tea scent).

*Lasting quality.*—On the plant and as cut flower—long.

Genital organs:

*Stamens, anthers.*—Medium size; many. Color—Antimony Yellow, Plate 15. Arrangement—regular around styles.

*Stamens, filaments (threads).*—Medium length. Color — Pomegranate Purple, Plate 12.

*Pollen.*—Color—Pinard Yellow, Plate 4.

*Styles.*—Bunched uneven length; medium length; thin.

*Stigmas.*—Color—Picric Yellow, Plate 4.

*Ovaries.*—All enclosed in calyx.

*Plant*

Form: Bush.

Growth: Vigorous; upright.

Foliage: 3 to 5 leaflets.

*Size.*—Large.

*Quantity.*—Normal.

*Color.*—New foliage—upper side: Yellowish Oil Green, Plate 5, lightly overcast with Oxblood Red, Plate 1; under side: Oxblood Red, Plate 1, lightly overcast with Lettuce Green, Plate 5. Old foliage—upper side: Forest Green, Plate 17; under side: Light Bice Green, Plate 17.

*Shape.*—Oval pointed.

*Texture.*—Upper side—glossy. Under side—smooth. Ribs and veins—prominent.

*Edge.*—Serrated (saw toothed).

*Serration.*—Double; small; sharp.

*Leaf Stem.*—Color—Rainette Green, Plate 31. Under side—smooth.

*Stipules.*—Medium length; smooth.

*Disease resistance.*—Resistant.

Wood:

*New wood.*—Color—Yellowish Oil Green, Plate 5. Bark—smooth.

*Old wood.*—Color—Cress Green, Plate 31. Bark—smooth.

Thorns:

*Thorns.*—Quantity—on main stalks from base and on laterals from stalk—ordinary. Form — Narrow base; medium length; hooked downward. Color when young—Oxblood Red, Plate 1. Position—irregular.

*Prickles and short needles.*—None.

I claim:

A new and distinct variety of rose plant of the large-flowered polyantha class, characterized as to novelty by the sharp, clear and unique color tones of Spectrum Red overcast with Scarlet Red of the flowers, by the cupped form of the flowers which particularly accentuates the sharpness of color as aforeaid, by the unique central petaloids having a deep cut at the top with a white streak through the center by its freedom of growth and clustered habit of bloom in a true Floribunda manner, and by its hardiness and disease resistace, substantially as shown and described.

WILHELM KORDES.

No references cited.